(12) United States Patent
Martin

(10) Patent No.: US 6,733,764 B2
(45) Date of Patent: May 11, 2004

(54) IMMUNOSTIMULATOR ANTI-CANCER COMPOUNDS AND METHODS FOR THEIR USE IN THE TREATMENT OF CANCER

(76) Inventor: Alain Martin, 31 Country Club Dr., Ringoes, NJ (US) 08551

( * ) Notice: Subject to any disclaimer, the term of this patent is extended or adjusted under 35 U.S.C. 154(b) by 0 days.

(21) Appl. No.: 09/878,466

(22) Filed: Jun. 11, 2001

(65) Prior Publication Data

US 2002/0001573 A1 Jan. 3, 2002

Related U.S. Application Data

(60) Provisional application No. 60/211,622, filed on Jun. 14, 2000.

(51) Int. Cl.$^7$ ............................ A61K 31/05; A61K 39/39
(52) U.S. Cl. .................. 424/278.1; 424/85.1; 424/85.2; 424/130.1; 424/277.1; 514/34; 514/152; 514/154; 514/731; 514/733; 514/734
(58) Field of Search ............................ 424/277.1, 278.1, 424/85.1, 45.2, 130.1; 514/34, 152, 154, 731, 733, 734

(56) References Cited

U.S. PATENT DOCUMENTS 5,877,017 A * 3/1999 Boel et al. .................. 435/325
6,355,691 B1 * 3/2002 Goodman .................... 514/731

FOREIGN PATENT DOCUMENTS

WO 9423067 * 10/1994

OTHER PUBLICATIONS

Hong et al, Arch. Pharm. Res., 22, 638–641, 1999.*

* cited by examiner

*Primary Examiner*—David Saunders

(57) ABSTRACT

The present invention comprises a method for the treatment of cancerous tumors in mammals comprising the administration of an effective amount of an immunostimulator which enhances and potentiates the mammals own immune system to selectively attack and kill the cancerous cells. The immunostimulator, preferably urushiol, is administered in a pharmaceutically acceptable carrier and can be co-administered in conjunction with other immunostimulators, radiation therapy or other cytotoxic anti-cancer agents to further enhance their effect.

3 Claims, No Drawings

IMMUNOSTIMULATOR ANTI-CANCER COMPOUNDS AND METHODS FOR THEIR USE IN THE TREATMENT OF CANCER

RELATED APPLICATIONS

This utility application is based on a provisional application U.S. Ser. No. 60/211,622 filed on Jun. 14, 2000.

FIELD OF THE INVENTION

The invention relates generally to novel anti-cancer compounds and their use as immunostimulators to enhance the activity of macrophages and lymphoid cells in attacking tumors and other neoplastic tissue. In particular, the invention relates to the use of immunostimulator compounds together with traditional anti-cancer therapeutic methods to achieve synergistic results.

BACKGROUND OF THE INVENTION

Cancer is the second-leading cause of death after cardiovascular disease in the United States. More than one million people were diagnosed with cancer last year and over 500,000 die of it each year. Surgery, radiation, and systemic drugs are the most common, traditional forms of cancer treatments. Localized cancer tumors are removed surgically or reduced through radiation. Tumors that have metastasized are treated with systemic therapies such as drugs, hormones, anti-hormones, and biological agents. Cytotoxic agents are the dominant therapy, however the problem with the use of these agents known as chemotherapy is that it can often cause cellular and organ damage to non-cancerous tissues, producing secondary problems including infections and death. Anti-cancer drugs are highly toxic causing serious and dose limiting side effects such as nausea, vomiting, neutropenia, and hair loss, organ damage, and death.

Basal cell carcinoma (BCC) is the most common malignant tumor of the skin, accounting for most of the approximately one million new cases of skin cancer diagnosed each year in the United States. See Miller, D. L., et al., *Nonmelanoma Skin Cancer in the United States: Incidence*. J. Am. Acad. Dermatol., 1994, Vol. 30, pp. 774–8. In selecting the most appropriate treatment, there are a number of variables that must be taken into account including histopathological type; size, location, and duration; and whether the lesion is primary or recurrent. The current treatment options of basal cell carcinoma is primarily surgical including Mohs micrographic surgery, simple excision, curettage and electro-dessication, or cryosurgery. See Drake, L. A., et al., *Guidelines of Care for Basal Cell Carcinoma*. J. Am. Acad. Dermatol., 1992, Vol. 26, pp. 117–20.

Accumulating data has shown that therapy with immune response modifying agents may offer effective therapy for basal cell carcinoma. Patients with noduloulcerative and superficial basal cell carcinoma have been shown to be responsive to the intra-lesional, immunonomodulation with interferon alfa-2b. See Cornell, R. C., et al., *Intra-lesional Therapy for Basal Cell Carcinoma*. J. Am. Acad. Dermatol., 1990, Vol. 23, pp. 694–700; and, Greenway, H. T., et al., *Treatment of Basal Cell Carcinoma with Intra-lesional Interferon*. J. Am. Acad. Dermatol., 1986, Vol. 15, pp. 437–43. Interferon can increase cell surface antigenicity of neoplastic cells, improving cell-mediated cytotoxicity leading to cell destruction. Imiquimod 5% cream has recently been shown in a randomized, double-blind pilot trial to show clinical efficacy in the treatment of nodular or superficial BCCS. See Beutner, K. R., et al., *Therapeutic Response of Basal Cell Carcinoma to the Immune Response Modifier Imiquimod 5% Cream*. J. Am. Acad. Dermatol., 1999, Vol. 41, pp. 1002–7. Topically applied imiquimod has been shown to induce local proliferation of interferon and other cytokines that may be important mediators of tumor clearance. Fifteen of 15 patients who applied imiquimod cream either three times a week, once daily, or twice daily achieved complete clinical and histologic clearing of superficial BCCs. Beutner K R et al., supra.

Many cancer cells evade the immune system. They can then proliferate and spread throughout the body, eventually killing the host. Angiogenesis (capillary growth to the tumor) in melanoma and various carcinomas often correlates with the likelihood of the development of metastases and the prognosis in such patients. Immunostimulators that can also serve as a form of anti-angiogenic therapy would inhibit the growth of the cancer and its spread. Immunostimulators activate the immune system to search out and kill the spreading tumor cells. Immunostimulators can also help the body develop an immunological memory in the host and in this way can potentiate the immune system. Exemplary immunostimulators include cytokines, and lipopolysaccharides obtained from the cell walls of Gram-negative bacteria. Specific immunostimulators have been utilized in the treatment of ovarian or pancreatic tumors. Immunostimulators can also activate macrophages, but unfortunately, most immunostimulators developed to date have been less than 100% effective. Most will enhance the immune system but all of them lack the ability to stimulate an immunological memory to the tumor cells. Other suitable secondary immunostimulators include bacillus Calmette-Guérin, immunoglobulin, alpha-interferon, interleukin-2, synthetic agents such as levamisole and isoprinosine and mixtures thereof.

Urushiol is an immunostimulator which has been shown to invoke an inflammatory response, stimulating white blood cells and other components of the immune system to localize at a particular site. In the past several investigators have attempted to use urushiol as an anti-cancer agent to treat various cancer cell lines. In all cases, the treatment failed to kill the tumors or inhibit the growth of the tumors or tumor cell lines in comparison to adriamycin. What the investigators failed to realize is that urushiol is a weak anti-cancer agent, but a strong immunostimulator, which can be used in combination with other therapies. To date, no one has used or teaches the use of urushiol as an immunostimulator that enhances current therapies. The compound occurs naturally and is the main component of the irritant oil in the leaves of poison ivy, *Toxicodendron radicans*, poison oak *T. diversilobum*, and other plants of the genus Toxicodendron. See Hill, et al., J. Am. Chem. Soc., 1934, Vol. 56, p. 2736. It is a mixture of several compounds which are derivatives of catechol and unsaturated $C_{15}$ or $C_{17}$ side chains and which, upon hydrogenation, yield the same 3-pentadecylcatechol, q.v. or 3-heptadecylctechol. Intralesional therapy of urushiol into basal cell carcinoma will produce a local inflammatory response, stimulating immunologically-mediated cells to areas of malignant and premalignant cells. Urushiol in combination with tumor-associated antigens, would enhance the activity of the antigen.

The unequivocal demonstration that tumor-associated peptides are recognized by cytolytic T-lymphocytes (CTLs) has stimulated worldwide efforts to identify as many of such antigens as possible and their human leucocyte antigen (HLA) restricted presentation by various tumor types. A widely used strategy for the identification of T-cell epitopes is to predict HLA-restricted peptides out of the sequence of tumor-associated proteins by the use of appropriate algorithms. These peptides were used for the stimulation of T-cells, which were then tested for recognition of tumor cells. The main reason for the frequent failure of this approach is that the predicted peptides are not naturally processed and are therefore not relevant for tumor-cell recognition. Therefore, a biochemical strategy to obviate these failures has been developed. In a first step, the potential peptides are predicted, synthesized, and analyzed by HPLC-linked mass spectrometry. In a second step, the naturally produced peptides are eluted from the MHC class I molecules of solid tumors or of tumor cell lines. A mixture of predicted synthetic peptides is then checked against the great number of eluted peptides using a specially adapted computer software. Thus identified, naturally occurring tumor peptides are used for the activation of T-cells, and the T-cells are tested for tumor cell recognition.

Another promising strategy to improve the prediction of relevant cytotoxic T-cell epitopes comprises the combination of HLA-motif prediction and determination of the cleavage specificity of proteasomes. Proteasomal cleavage is essential for the generation of peptides that are delivered to MHC class I molecules for presentation on the cell surface. To analyze the proteasomal specificity, the protein of interest is degraded in vitro by purified proteasome particles. The cleavage products are purified by HPLC and analyzed further by a combination of Edman degradation and mass spectometry. This approach provides a basis for predicting proteasomal degradation products from which peptides are sampled by MHC class I molecules.

Epimmune Inc., San Diego, Calif., has created altered tumor protein sequences that could enhance the effectiveness of cancer vaccines. Details of the technology were disclosed at the "3$^{rd}$ Colloquium on Cancer Vaccines and Immunotherapy" in Abaco, Bahamas which is hereby incorporated by reference. Using a defined set of rules, specific amino-acid sequences contained within epitopes of natural tumor antigens are altered. Epitopes are the portions of the tumor antigens that act like red flags to alert the immune system and stimulate an attack on the tumor cells. The epitope analogs are then tested for their ability to induce cytotoxic T-cell responses. These immune responses are important because cytotoxic T-cells are capable of destroying cancerous or infected cells.

The present invention then, combines urushiol as an immunostimulator with various types of analogs, including the heterocyclic analogs described herein and selected native-sequence epitopes, from multiple tumor-associated antigens to maximize the number of T-cells activated for each tumor antigen. By using analogs in epitope-based vaccines with urushiol, it is possible to activate T-cells that would not otherwise be stimulated to attack the tumor. Combining these therapies, even more potent vaccines can be created against cancer and infectious diseases.

SUMMARY OF THE INVENTION

The present invention comprises the administration of immunostimulator compositions for the treatment of cancer. In particular, immunostimulator compositions comprising urushiol are administered to invoke an inflammatory response in the tumor which stimulates white blood cells and other components of the immune system to recognize and attack the malignant cells.

DETAILED DESCRIPTION OF THE INVENTION

The present invention comprises anti-cancer agents and compositions comprising an immunostimulator known as urushiol. The urushiol compound has the formula:

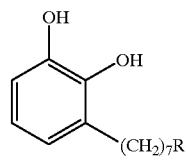

wherein R is selected from the group comprising $(CH_2)_7CH_3$, $CH=CH(CH_2)_5CH_3$, $CH=CHCH_2CH=CH(CH_2)_2CH_3$, $CH=CHCH_2CH=CHCH=CHCH_3$ and $CH=CHCH_2CH=CHCH_2CH=CH_2$ Urushiol occurs naturally and is the main constituent of the irritant oil in the leaves of the poison ivy, *Toxicodendron radicans*, poison oak *T. diversilobum* and other plants of the genus Toxicodendron Hill et. al., J. Am. Chem. Soc., 1934, Vol. 56, p. 2736. It is a mixture of several compounds which are derivatives of catechol and unsaturated $C_{15}$ or $C_{17}$ side chains and which, upon hydrogenation, yield the same 3-pentadecylcatechol, q.v. or 3-heptadecylctechol.

By injecting urushiol into tissue, an inflammatory response will result. White blood cells will then enter the site to attack the antigen that initiated that response. By combining urushiol with other immunostimulators or with other cancer agents, the ability of white blood cells to kill tumors is enhanced. The urushiol compounds can be united with other immunostimulators to produce a new chemical agent. Urushiol is a potent immunostimulator and is also an anti-angiogenic agent. Urushiol will elicit a life long immunological response when used.

The present invention then, comprises a method for treating cancerous tumors in a mammal in need of such treatment by enhancing the immune system to attack the tumors. The invention also is a method for enhancing the therapeutic effectiveness of other current drug and radiation therapies. The treatment comprises the use of injected urushiol in tumors, prior to, in conjunction with, or after treatment with cancer drugs, other immunostimulators, radiation therapies and other forms of cancer treatments. Suitable secondary immunostimulators include cytokines, tumor-associated proteins and antigens, cancer vaccines, ultra-sound, photo-reactive compounds, anthracyclines, lipopolysaccharides, bacillus Calmette-Guérin, immunoglobulins, alpha-interferon, interleukin-2, synthetic agents such as levamisole or isoprinosine and mixtures thereof. In particular, the urushiol can be administered together with an anti-cancer agent such as: nitrogen mustards, ethyleneamines and methylmelamines, alkyl sulfonates, nitrosoureas, triazenes, folic acid analogs, pyrimidine analogs, purine analogs and related inhibitors, vinca alkaloidss, epipodophyllotoxins, antibiotics, biological response modifiers, alpha-interferon, platinum coordination complexes, anthracenedione, substituted-urea, methylhydrazine derivatives, adrenocortical suppressants, adrenocorticossteroids, progestins, estrogens, antiestrogen, androgens, antiandrogens, imiquimod, solvents that destroy cancer cells causing the release of cancer antigens and mixtures thereof.

The following examples are provided to more specifically define and set forth the benefits of the compounds and therapy of the present invention. It is to be understood however, that they are for illustrative purposes only and should not be construed as limiting the spirit and scope of the invention as later set forth and recited in the claims that follow.

EXAMPLE 1

Various human cancer cell lines were used and cultured with RPMI 1640 containing 10% fetal calf serum. The assay was performed by a method developed by Kim et al 1996. A cell suspension (3–40,000 cells/ml) was made in culture medium and inoculated to each well of a 96 well micro-titer plate. One day after plating, the compounds were added and the cells were incubated for 48 hours in a $CO_2$ incubator. The cells were fixed and stained. Optical density was measured with a microtiter plate reader at 540 nm. Growth inhibition was calculated according to standard methods known in the art. The administration of urushiol by itself showed very poor growth inhibition in comparison to adriamycin. The combination of urushiol and adriamycin however, resulted in a growth inhibition that was far superior to either of the compounds by themselves, producing a synergistic cell growth inhibition effect.

EXAMPLE II

A fifty-one (51) year old male in good health was infected with poison ivy on his legs. One of his legs contained two dark pre-melanoma or melanoma patches approximately ten inches apart. The poison ivy resulted in swelling and the formation of blisters. The poison ivy by itself did not reduce or eliminate either of the dark pre-melanoma or melanoma patches on his leg. The destruction of the other dark patch was enhanced by a sunburn, produced by UV light since urushiol will produce oxygen radicals, known to kill cells. UV light also produces oxygen radicals which destroy cells releasing tumor antigens, and three days after receiving the sunburn on the second patch, the area turned very red with erythema, as if infected. Approximately 7 days later, the dark area disappeared, eventually leaving only normal skin. Without being bound to any theory, it is believed that the poison ivy-derived urushiol in combination with UV light, destroyed the cancerous cells forming the dark patch of skin which totally disappeared. Surgical removal of the second site substantiated the fact that urushiol acted as an anti-angiogenesis factor, killing local capillaries. It also enhanced the lines of demarcation between pre-melanoma cells and normal cells.

What I claim is:

1. A method for the enhancement of the immune system to attack cancerous tumors and inhibit capillary growth to tumors in a mammal comprising the administration of an effective amount of urushiol in a pharmaceutically acceptable carrier together with the co-administration of one or more secondary immunostimulators selected from the group consisting of cytokines, tumor-associated proteins and antigens, tumor vaccines, lipopolysaccharides, Bacillus Calmette-Gurin, immunoglobulin, alpha-interferon, interleukin-2, levamisole, isoprinosine, and mixtures thereof.

2. A method for the enhancement of anti-cancer agents for the treatment of cancerous tumors in a mammal comprising the administration of an effective amount of urushiol together with an anti-cancer agent selected from the group consisting essentially of adriamycin, ultra-sound, photo-reactive compounds, anthracyclines, nitrogen mustards, ethyleneamines, methylmelamines, alkyl-sulfonates, nitrosoureas, triazenes, folic acid analogs, pyrimidine analogs, purine analogs and related inhibitors, vinca alkaloids, epipodophyllotoxins, antibiotics, tumor-associated proteins and antigens, biological response modifiers, alpha-interferon, platinum coordination complexes, anthracenedione, substituted-ureas, methylhydrazine derivatives, adrenocortical suppressants, adrenocorticosteroids, progestins, estrogens, anti-estrogens, androgens, anti-androgens, solvents that destroy cancer cells causing the release of cancer antigens, and mixtures thereof.

3. A method for the treatment of cancer through the enhancement of the immune system to attack cancerous tumor cells and the inhibition of capillary growth to tumors through the simultaneous use of immunostimulators and anti-cancer agents to kill said cells, said method comprising (i) the administration of an effective amount of urushiol in a pharmaceutically acceptable carrier together with, (ii) the co-administration of one or more secondary immunostimulators selected from the group consisting of cytokines, tumor-associated proteins and antigens, tumor vaccines, lipopolysaccharides, Bacillus Calmette-Gurin, immunoglobulin, alpha-interferon, interleukin-2, levamisole, isoprinosine, and mixtures thereof together with, (iii) the co-administration of an anti-cancer agent selected from the group consisting essentially of adriamycin, surgery, ultra-sound, photo-reactive compounds, anthracyclines, nitrogen mustards, ethyleneamines, methylmelamines, alkyl-sulfonates, nitrosoureas, triazenes, folic acid analogs, pyrimidine analogs, purine analogs and related inhibitors, vinca alkaloids, epipodophyllotoxins, antibiotics, biological response modifiers, platinum coordination complexes, anthracenedione, substituted-ureas, methylhydrazine derivatives, adrenocortical suppressants, adrenocorticosteroids, progestins, estrogens, anti-estrogens, androgens, anti-androgens, solvents that destroy cancer cells causing the release of cancer antigens, and mixtures thereof.

* * * * *